(12) United States Patent
Kathirgamanathan

(10) Patent No.: US 7,597,926 B2
(45) Date of Patent: Oct. 6, 2009

(54) ELECTROLUMINESCENT QUINOLATES

(75) Inventor: Poopathy Kathirgamanathan, Middlesex (GB)

(73) Assignee: South Bank University Enterprises Ltd. (GB)

( * ) Notice: Subject to any disclaimer, the term of this patent is extended or adjusted under 35 U.S.C. 154(b) by 703 days.

(21) Appl. No.: 11/140,338

(22) Filed: May 27, 2005

(65) Prior Publication Data
US 2006/0003089 A1 Jan. 5, 2006

Related U.S. Application Data

(63) Continuation of application No. 09/857,300, filed as application No. PCT/GB99/04024 on Dec. 1, 1999, now abandoned.

(30) Foreign Application Priority Data

Dec. 2, 1998 (GB) .................... 9826406.2

(51) Int. Cl.
*B05D 5/06* (2006.01)

(52) U.S. Cl. .......... 427/66; 540/575; 540/472; 540/556; 427/64; 427/58; 427/240

(58) Field of Classification Search ......... 540/575
See application file for complete search history.

(56) References Cited

U.S. PATENT DOCUMENTS 5,166,341 A * 11/1992 Kon et al. ............... 540/575

OTHER PUBLICATIONS

Hensen et al, Preparation of N- or O-Chloromethylsilyl Derivatives of the Amines 1, 2, 3, 4-Tetrahydro-1, 10-Phenanthroline and 8-Hydroxyquinoline, 1981, Journal of Organometallic Chemistry, vol. 290, pp. 17-23.*

Junji Kido, et al., Multilayer White Light-Emitting Organic Electroluminescent Device, Science, Mar. 3, 1995, vol. 267, pp. 1332-1334.

* cited by examiner

*Primary Examiner*—Michael Barr
*Assistant Examiner*—Andrew Bowman
(74) *Attorney, Agent, or Firm*—Goodwin Procter LLP

(57) ABSTRACT

Lithium quinolate is an electroluminescent material which emits light in the blue region of the spectrum.

7 Claims, 7 Drawing Sheets

ELECTROLUMINESCENT QUINOLATES

CROSS REFERENCE TO RELATED APPLICATIONS

This application is a continuation of application Ser. No. 09/857,300 filed Jun. 1, 2001, now abandoned, which is a national stage application of PCT/GB99/04024 filed Dec. 1, 1999 which claims priority of UK Application No. 98/26406.2 filed Dec. 2, 1998, all of which are incorporated by reference herein.

The present invention relates to novel photoluminescent and electroluminescent materials.

Aluminium quinolate is a known photoluminescent and electroluminescent material and emits light in the red area of the spectrum. In order to obtain light of a different wavelength dopants and/or dyes have been added to the aluminium quinolate. Structures have also been made with a layer containing dyes in contact with the aluminium quinolate layer but aluminium quinolate and structures based on aluminium quinolate have a relatively low efficiency.

In an article by Takeo Wakimoto et al in Applied Surface Science 113/114(1997) 698-704 electroluminscent cells are disclosed in which aluminium quinolate is used as the emitter and which is doped by quinacrodine derivatives which are fluorescent dyes to change the colour of the emitted light.

Electroluminescent devices can be made as described in an article by K. Nagayama et al in the Jpn. Journal of Applied Physics vol. 36 pps. 1555-1557.

The obtaining of blue light in an electroluminescent material is required to enable the complete range of colours to be obtained in devices incorporating such materials.

We have now obtained a novel electroluminescent material which emits blue light.

One aspect of the invention is lithium quinolate.

Another aspect of the invention is a method of making a metal quinolate which comprises reacting a metal alkyl or a metal alkoxide with 8-hydroxy quinoline.

A further aspect of the invention is the provision of a structure which incorporates a layer of lithium quinolate and a means to pass an electric current through the lithium quinolate layer.

Although some metal quinolates are known hitherto lithium quinolate has not been made and it was surprising that it was photoluminescent and electroluminescent in the blue spectrum.

Aluminium and other known metal quinolates are made by the reaction of a metal salt with 8-hydroxyquinoline.

In the method of the invention the metal alkyl or alkoxide is preferably reacted in the liquid phase with the 8-hydroxyquinoline. The metal compound can be dissolved in an inert solvent added to the 8-hydroxyquinoline. The metal quinolate can be separated by evaporation or when a film of the metal quinolate is required, by deposition onto a suitable substrate.

The preferred alkyls are ethyl, propyl and butyl with n-butyl being particularly preferred. With metal alkoxides he preferred alkoxides are ethoxide, propoxides and butoxides. The method is particularly suitable for the preparation of group I, II and III metals such as lithium, sodium potassium, zinc, cadmium and aluminium alkoxides.

Lithium quinolate can be synthesised by the reaction, in an inert solvent, e.g. acetonitrile, of 8-hydroxyquinoline with a lithium alkyl e.g. n-butyl lithium. The lithium quinolate is an off white or white solid at room temperature.

As well as the lithium salt of 8-hydroxyquinoline, the term quinolate in this specification includes salts of substituted 8-hydroxyquinoline

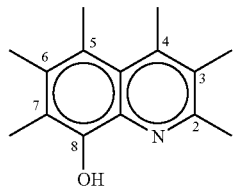

where the substituents are the same or different in the 2, 3, 4, 5, 6 and 7 positions and are selected from alky, alkoxy, aryl, aryloxy, sulphonic acids, esters, carboxylic acids, amino and amido groups or are aromatic, polycyclic or heterocyclic groups.

Alkali metal alkyls are difficult compounds to handle practically as they are highly reactive and can catch fire spontaneously in air. For this reason they would not normally be chosen as reactants.

An electroluminescent device comprises a conductive substrate which acts as the anode, a layer of the electroluminescent material and a metal contact connected to the electroluminescent layer which acts as the cathode. When a current is passed through the electroluminescent layer, the layer emits light.

Preferably the electroluminescent devices of the invention comprise a transparent substrate, which is a conductive glass or plastic material which acts as the anode, preferred substrates are conductive glasses such as indium tin oxide coated glass, but any glass which is conductive or has a conductive layer can be used. Conductive polymers and conductive polymer coated glass or plastics materials can also be used as the substrate. The lithium quinolate can be deposited on the substrate directly by evaporation from a solution in an organic solvent. Any solvent which dissolves the lithium quinolate can be used e.g. acetonitrilc.

A preferred method of forming a metal quinolate film e.g. useful in electroluminescent devices comprises forming the metal quinolate in situ by sequential dip coating the substrate with the film e.g. the substrate is dipped or otherwise coated with a solution of the metal alkyl or alkoxide to form a film on the surface and then dipped or otherwise coated with 8-hydroxyquinoline or substituted 8-hydroxyquinoline and the metal quinolate film is formed on the substrate surface.

For example to form a film of lithium quinolate the film or layer of lithium quinolate is deposited by in situ dip coating i.e. the substrate, such as a glass slide, is dipped into or otherwise contacted with a solution of an alkyl lithium e.g. n-butyl lithium and then immersed in or contacted with a solution of hydroxyquinoline, a layer of lithium quinolate is then formed on the substrate.

Alternatively the material can be deposited by spin coating or by vacuum deposition from the solid state e.g. by sputtering or any other conventional method can be used.

To form an electroluminescent device incorporating lithium quinolate as the emissive layer there can be a hole transporting layer deposited on the transparent substrate and the lithium quinolate is deposited on the hole transporting layer. The hole transporting layer serves to transport; holes and to block the electrons thus preventing electrons from moving into the electrode without recombining with holes. The recombination of carriers therefore mainly takes place in the emitter layer.

Hole transporting layers are used in polymer electroluminescent devices and any of the known hole transporting materials in film form can be used.

The hole transporting layer can be made of a film of an aromatic amine complex such as poly(vinylcarbazole), N,N'-diphenyl-N,N'-bis(3-methylphenyl)-I,I'-biphenyl-4,4'-di-amine (TPD), polyaniline etc.

Optionally dyes such as fluorescent laser dyes, luminescent laser dyes can be included to modify the colour spectrum of the emitted light.

The lithium quinolale can be mixed with a polymeric material such as a polyolefin e.g. polyethylene, polypropylene etc. and preferably polystyrene. Preferred amounts of active material in the mixture is from 95% to 5% by weight of active material and more preferably 25 to 20% by weight.

The hole transporting material can optionally be mixed with the lithium quinolate in a ratio of 5-95% of the lithium quinolate to 95 to 5% of the hole transporting compound. In another embodiment of the invention there is a layer of an electron injecting material between the cathode and the lithium quinolate layer, this electron injecting layer is preferably a metal complex such as a different metal quinolate e.g. an aluminium quinolate which will transport electrons when an electric current is passed through it. Alternatively the electron injecting material can be mixed with the lithium quinolate and co-deposited with it.

In another embodiment of the invention there is a layer of an electron transporting material between the cathode and the lithium quinolate layer, this electron transporting layer is preferably a metal complex such as a metal quinolate e.g. an aluminium quinolate which will transport electrons when an electric current is passed through it. Alternatively the electron transporting material can be mixed with the lithium quinolate and co-deposited with it.

Optionally dyes such as fluorescent laser dyes, luminescent laser dyes can be included to modify the colour spectrum of the emitted light and also enhance the photoluminescent and electroluminescent efficiencies.

In a preferred structure there is a substrate formed of a transparent conductive material which is the anode on which is successively deposited a hole transportation layer, the lithium quinolate layer and an electron transporting layer which is connected to the anode. The anode can be any low work function metal e.g. aluminium, calcium, lithium, silver/magnesium alloys etc.

The invention is further described with reference to the examples.

EXAMPLE 1

Lithium 8-hydroxyquinolate Li($C_9H_6ON$)

2.32 g (0.016 mole) of 8-hydroxyquinoline was dissolved in acetonitrile and 10 ml of 1.6 M n-butyl lithium (0.016 mole) was added. The solution was stirred at room temperature for one hour and an off white precipitate filtered off. The precipitate was washed with water followed by acetonitrile and dried in vacuo. The solid was shown to be lithium quinolate.

EXAMPLE 2

Lithium 8-hydroxyquinolate Li($C_9H_6ON$)

A glass slide (Spectrosil UV grade) was dipped into a solution of n-butyl lithium in acetonitrile for four seconds and then in immersed in a solution of 8-hydroxyquinoline for four seconds. A thin layer of lithium quinolate was easily seen on the glass.

EXAMPLE 3

Magnesium 8-hydroxyquinolate Mg($C_2H6ON$)$_2$

8-Hydroxyquinoline (5.0-g; 0.0345 mole) was dissolved in 2N acetic acid (150 ml) by heating at 70-80° C. Magnesium sulphate (2.5 g; 0.020 mole) was dissolved in water (100 ml) heated to 60° C. and basified with ammonia. Oxine solution was added to the mechanically stirred, basified magnesium sulphate solution at 60° C. and excess ammonia added until the pH of the solution was 9.5. The yellow precipitate was digested at 60° C. for a further 10 minutes, cooled and filtered under suction, washed with dilute ammonia and dried in vacuo at 100° C. for several hours. Yield 5.06. g

EXAMPLE 4

Zinc 8-hydroxyquinolate Zn($C_2H6ON$)$_2$

The above procedure was employed using 8-hydroxyquinoline (5.0 g; 0.0345 mole) and zinc chloride (2.8 g; 0.020 mole). The yellow precipitate was filtered, washed with dilute ammonia and dried in vacuo at 75° C. for 6 hours. Yield 6.48 g

EXAMPLE 5

Calcium 8-hydroxyquinolate Ca($C_2H6ON$)$_2$

Using similar procedure with 8-hydroxyquinoline (5.0 g; 0.0345 mole) and calcium chloride (3.8 g; 0.034 mole). calcium 8-hydroxyquinolate was obtained as a yellow powder 5.60 g yield.

EXAMPLE 6

Sodium 8-hydroxyquinolate Na($C_2H6ON$)

8-Hydroxyquinoline (5.0 g; 0.0345 mole) was dissolved in 2% sodium hydroxide solution (100 ml) and heated to 60° C. The solution was stirred at this temperature for 30 minutes and the homogeneous solution was cooled to room temperature. No solid was separated out. Therefore the solution was concentrated in a rotary evaporator and the concentrated solution was cooled to give a pale yellow solid. The solid was filtered under suction washed with small amounts of sodium hydroxide solution and dried in vacuo at 80° C. for several hours. The sodium 8-hydroxyquinolate is soluble in water. Yield 3.6 g.

EXAMPLE 7

Potassium 8-hydroxyquinolate K($C_2H6ON$)

Potassium 8-hydroxyquinolate was also made from 8-hydroxyquinoline (2.0 g; 0.0138 mole) in dry tetrahydrofuran (50 ml) and potassium tert-butoxide (2.32 g; 0.021 mole). The solution was heated to become homogeneous and cooled to room temperature to give a yellow solid yield 2.2 g.

The photoluminescent efficiency and maximum wavelength of the PL emission of the lithium quinolate was measured and compared with other metal quinolates and the results shown in Table 1. Photoluminescence was excited using 325 mn line of Liconix 4207 NB, He/Cd laser. The laser power incident at the sample (0.3 mWcm-2) was measured by a Liconix 55PM laser power meter. The radiance calibration was carried out using Bentham radiance standard (Bentham SRS8, Lamp current 4,000 A), calibrated by National Physical laboratories, England. The PL studies were carried out on samples or films. The Spectra are attached as FIGS. 2 to 7.

TABLE 1

| Complex | CIE x, y | $\lambda_{max}$ (PL)/nm | Absolute Photoluminescent Efficiency % $\eta$PL |
|---|---|---|---|
| Liq | 0.17, 0.23 | 465 | 48 |
| Naq | 0.19, 0.31 | 484 | 32 |
| Kq | 0.19, 0.33 | 485 | 36 |
| Baq$_2$ | 0.16, 0.29 | 479 | 7 |
| Caq$_2$ | 0.21, 0.37 | 482 | 24 |
| Mgq$_2$ | 0.22, 0.46 | 500 | 43 |
| Znq$_2$ | 0.26, 0.51 | 518 | |
| Alq$_3$ | 0.32, 0.56 | 522 | 27 |

EXAMPLE 8

An electroluminescent device of structure shown in FIG. 1 was fabricated using aluminium quinolate and lithium quinolate as the electroluminescent layer and the electroluminescent properties measured. Referring to FIG. 1 (2) is an ITO layer, (4) is a TPD layer (hole transporting layer) (60 nm), (1) is the lithium quinolate layer (5) is an aluminium quinolate layer and (3) is aluminium (900 nm).

1. Device Fabrication

An ITO coated glass piece (1×1 cm$^2$ cut from large sheets purchased from Balzers, Switzerland) had a portion etched out with concentrated hydrochloric acid to remove the ITO and was cleaned and placed on a spin coater (CPS 10 BM, Semitec, Germany) and spun at 2000 rpm for 30 seconds, during which time the solution of the electroluminescent compound was dropped onto it dropwise by a pipette.

Alternatively the electroluminescent compound was vacuum evaporated onto the ITO coated glass piece by placing the substrate in a vacuum coater and evaporating the electroluminescent compound at $10^{-5}$ to $10^{-6}$ torr onto the substrate.

The organic coating on the portion which had been etched with the concentrated hydrochloric acid was wiped with a cotton bud.

The coated electrodes were stored in a vacuum desiccator over calcium sulphate until they were loaded into a vacuum coater (Edwards, $10^{-6}$ torr) and aluminium top contacts made. The active area of the LED's was 0.08 cm$^2$ by 0.1 cm$^2$ the devices were then kept in a vacuum desiccator until the electroluminescence studies were performed.

The ITO electrode was always connected to the positive terminal. The current vs. voltage studies were carried out on a computer controlled Keithly 2400 source meter.

Electroluminescence spectra were recorded by means of a computer controlled charge coupled device on Insta Spec photodiode array system model 77112 (Oriel Co. Surrey, England)

The spectra are shown in the drawings.

In the spectra:

Figure 1:
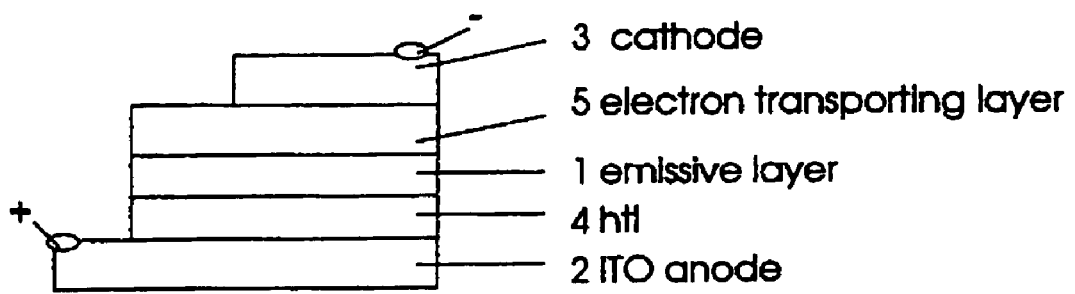
FIG. 1 is a schematic representation of an electroluminescent device in accordance with Example 8 in which (1) is a lithium quinolate layer, (2) is an ITO layer, (3) is aluminum (900 nm), (4) is a hole transporting layer and (5) is an aluminum quinolate layer.
Figure 2:
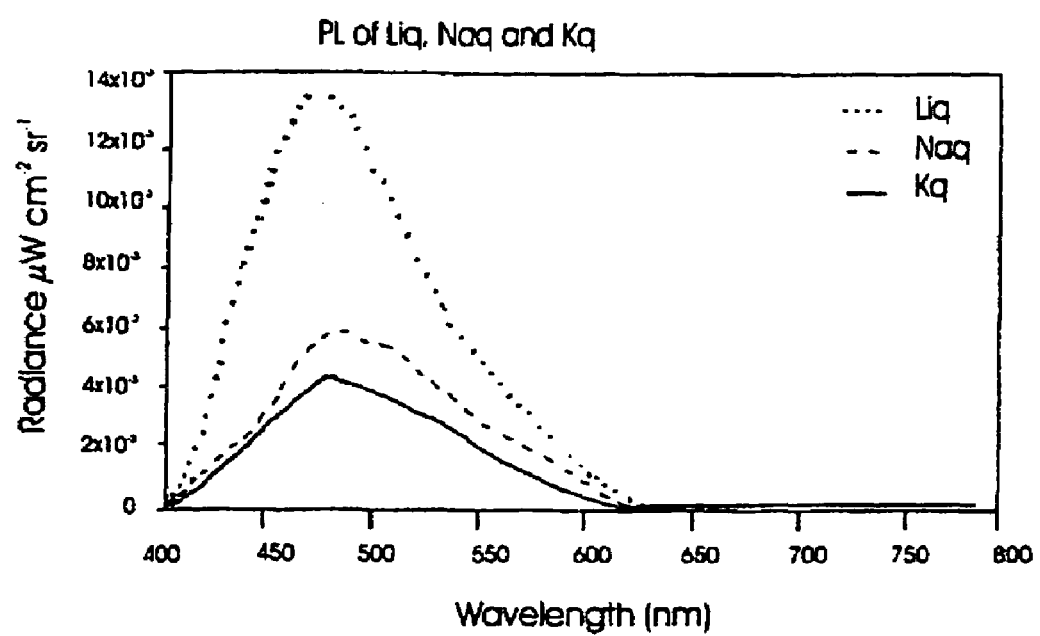
FIG. 2 shows the PL of lithium 8-hydroxyquinolate of Example 1 and the quinolates of Examples 6 and 7.
Figure 3:
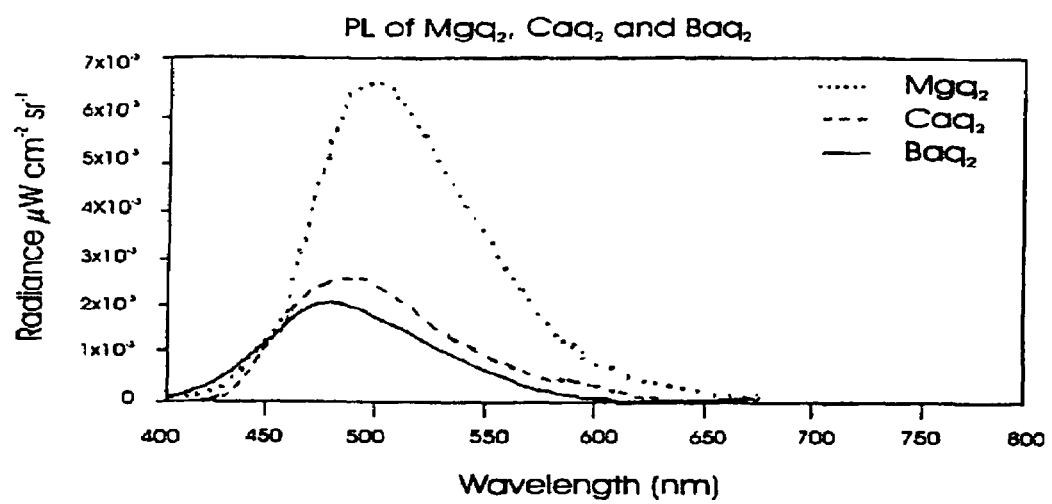
FIG. 3 shows the PL of quinolates of Examples 3 and 5 and that of barium quinolate made by the same method.
Figure 4:
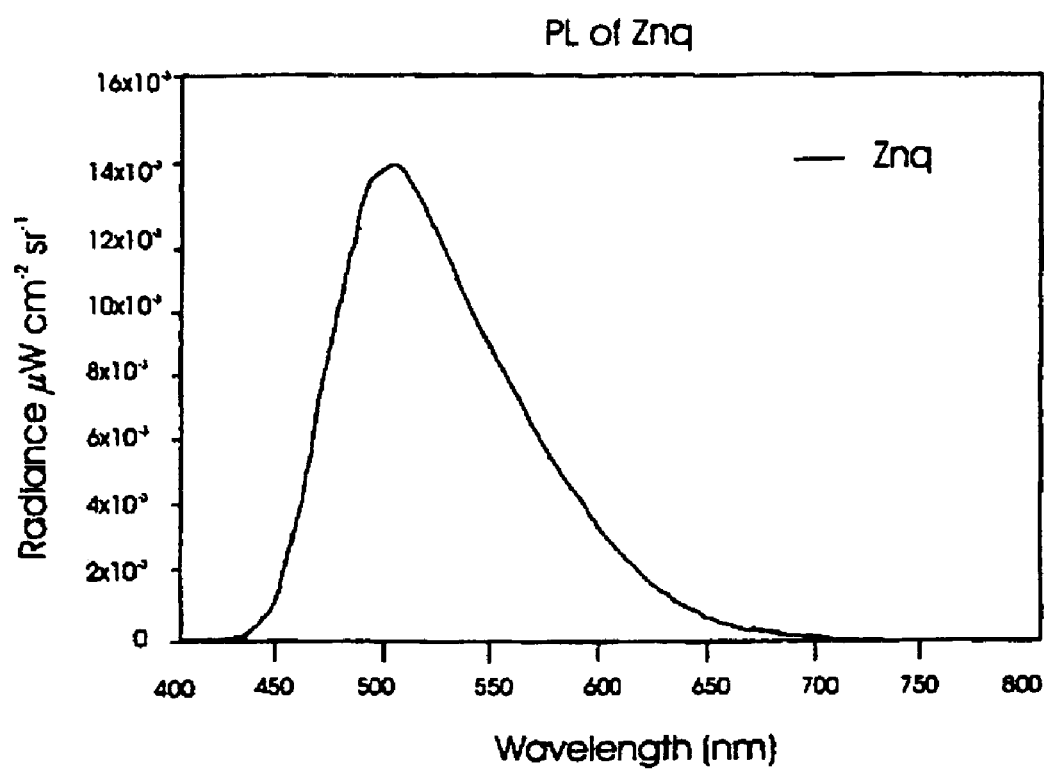
FIG. 4 shows the PL of zinc quinolate of Example 4
Figure 5:
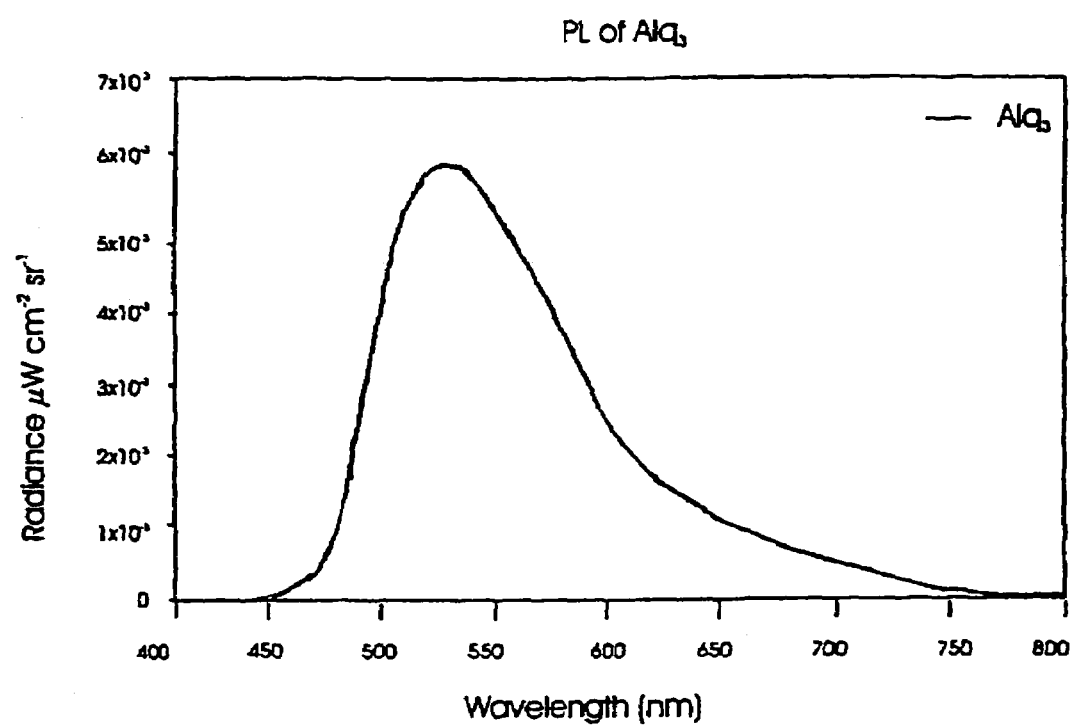
FIG. 5 shows the PL of commercially available aluminium quinolate.
Figure 6:
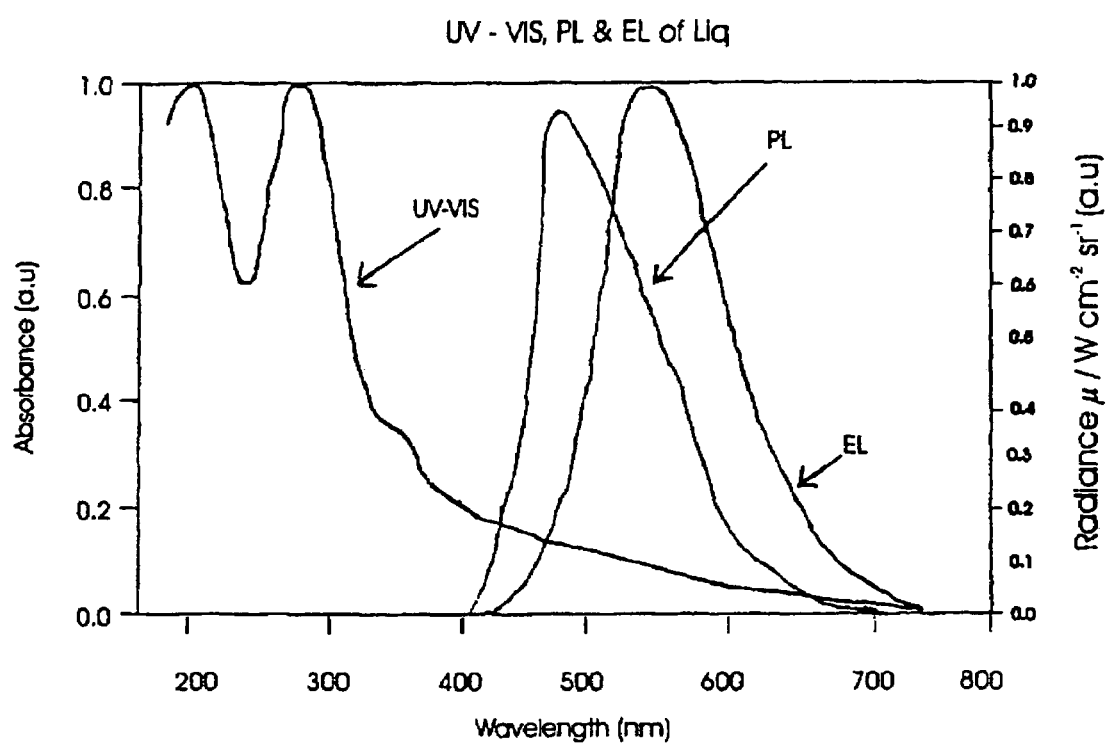
FIG. 6 shows the IV-VIS, PL and EL of lithium quinolate.
Figure 7:
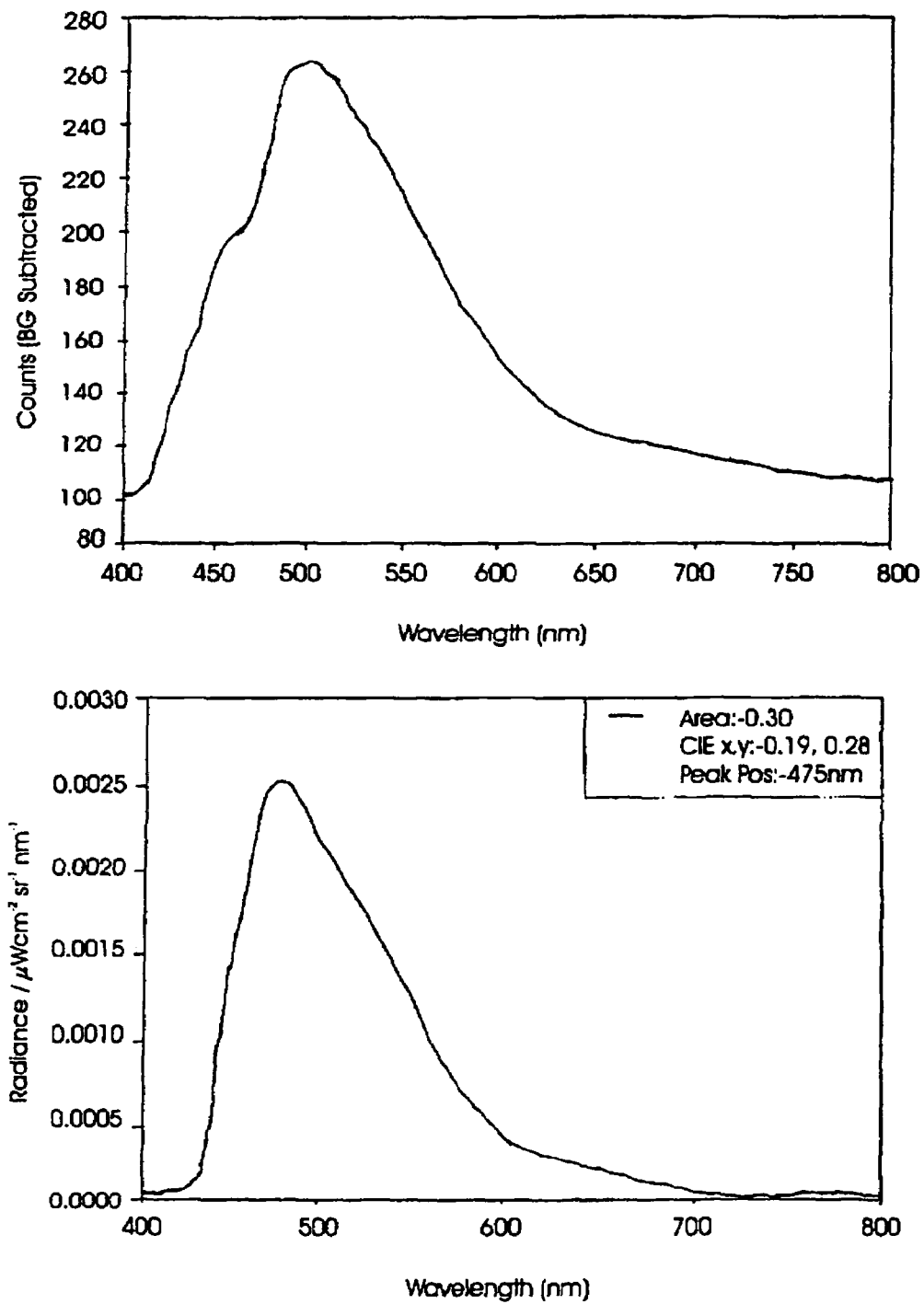
FIG. 7 shows the spectra of lithium quinolate of Example 2

I claim:

1. A method of making a lithium quinolate which is substituted or unsubstituted, said method comprising:
reacting a lithium alkyl or lithium alkoxide in a solvent comprising acetonitrile with an 8-hydroxy quinoline, the 8-hydroxy quinoline optionally having at least one substituent selected from the group consisting of alkyl, alkoxy, aryl, aryloxy, sulphonic acid, ester, carboxylic acid, amino, amido, aromatic, polycyclic and heterocyclic.

2. The method of claim 1, wherein said compound is unsubstituted lithium quinolate.

3. The method of claim 1, further comprising the step of forming the lithium quinolate or substituted lithium quinolate into a film or layer by spin coating onto a substrate.

4. The method of claim 1, further comprising the step of forming the lithium quinolate or substituted lithium quinolate into a film or layer by vacuum deposition onto a substrate.

5. The method of claim 2, further comprising the step of forming the lithium quinolate into a film or layer by spin coating onto a substrate.

6. The method of claim 2, further comprising the step of forming the lithium quinolate into a film or layer by vacuum deposition onto a substrate.

7. A method of making a lithium quinolate which is substituted or unsubstituted, said method comprising:
reacting a lithium alkyl or lithium alkoxide in a solvent comprising acetonitrile with an 8-hydroxy quinoline, the 8-hydroxy quinoline optionally having at least one alkyl substituent.

* * * * *

UNITED STATES PATENT AND TRADEMARK OFFICE
CERTIFICATE OF CORRECTION

PATENT NO. : 7,597,926 B2  Page 1 of 1
APPLICATION NO. : 11/140338
DATED : October 6, 2009
INVENTOR(S) : Poopathy Kathirgamanathan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1059 days.

Signed and Sealed this

Twenty-eighth Day of September, 2010

David J. Kappos
*Director of the United States Patent and Trademark Office*